US007981144B2

United States Patent
Geist et al.

(10) Patent No.: US 7,981,144 B2
(45) Date of Patent: Jul. 19, 2011

(54) IMPLANT EQUIPPED FOR NERVE LOCATION AND METHOD OF USE

(75) Inventors: Wyatt Drake Geist, Davie, FL (US); Christopher Walsh, Parkland, FL (US)

(73) Assignee: Integrity Intellect, Inc., Tamarac, FL (US)

( * ) Notice: Subject to any disclaimer, the term of this patent is extended or adjusted under 35 U.S.C. 154(b) by 828 days.

(21) Appl. No.: 11/534,129

(22) Filed: Sep. 21, 2006

(65) Prior Publication Data

US 2008/0125637 A1    May 29, 2008

(51) Int. Cl.
- *A61B 17/04* (2006.01)
- *A61B 17/84* (2006.01)
- *A61B 2/08* (2006.01)

(52) U.S. Cl. .......................................... 606/300; 606/76

(58) Field of Classification Search .................... 606/53, 606/60, 300, 76, 302, 328, 331; 411/402; 600/377, 424; 128/899
See application file for complete search history.

(56) References Cited

U.S. PATENT DOCUMENTS

| | | | |
|---|---|---|---|
| 2,704,064 A | 3/1955 | Fizzell et al. | |
| 4,713,506 A * | 12/1987 | Klink | 200/507 |
| 5,196,015 A | 3/1993 | Neubardt | |
| 5,284,153 A | 2/1994 | Raymond et al. | |
| 5,474,558 A | 12/1995 | Neubardt | |
| 6,499,488 B1 * | 12/2002 | Hunter et al. | 128/899 |
| 6,510,347 B2 * | 1/2003 | Borkan | 607/117 |
| 6,564,078 B1 * | 5/2003 | Marino et al. | 600/373 |
| 6,565,565 B1 * | 5/2003 | Yuan et al. | 606/272 |
| 6,796,985 B2 | 9/2004 | Bolger et al. | |
| 7,172,594 B2 * | 2/2007 | Biscup | 606/86 A |
| 2004/0243207 A1 * | 12/2004 | Olson et al. | 607/116 |
| 2005/0075578 A1 | 4/2005 | Gharib et al. | |
| 2005/0085743 A1 | 4/2005 | Hacker et al. | |
| 2005/0149035 A1 | 7/2005 | Pimenta et al. | |
| 2006/0025703 A1 * | 2/2006 | Miles et al. | 600/554 |
| 2006/0111767 A1 | 5/2006 | Olson et al. | |
| 2006/0200023 A1 | 9/2006 | Melkent et al. | |
| 2010/0106198 A1 * | 4/2010 | Adcox et al. | 606/301 |

OTHER PUBLICATIONS

Inter Ikea Systems B.V. ASPVIK Manual. (c) 2006. pp. 2.*

* cited by examiner

*Primary Examiner* — Eduardo C Robert
*Assistant Examiner* — David W Bates
(74) *Attorney, Agent, or Firm* — McHale & Slavin, P.A.

(57) ABSTRACT

The invention describes a surgical implant that is equipped to provide neurological data during and after implantation. Neurological monitoring ensures accurate insertion of the implant with minimal disturbance of neural structures. The implant includes at least one electrically conductive region that is utilized to determine the distance from and direction to a nerve with respect to the implant.

13 Claims, 3 Drawing Sheets

IMPLANT EQUIPPED FOR NERVE LOCATION AND METHOD OF USE

FIELD OF THE INVENTION

The invention generally relates to surgical implants and methods for their insertion; particularly to surgical implants and methods using an electrical potential to avoid nerve damage during surgical insertion of implants; most particularly to an implant having at least one electrically conductive region that is utilized to determine the distance from and direction to a nerve with respect to the implant.

BACKGROUND OF THE INVENTION

Pedicle screw fixation has become the favored mode of rigid internal fixation of the three vertebral columns of the spine. The use of pedicle screw-based instrumentation systems has steadily increased over the past three decades due to their superior biomechanical properties and higher bony fusion rates. However, violation of the pedicle medial wall or vertebral body while implanting these screws carries the risk of injury to neural, vascular, and visceral structures. For example, the screw body can break through the vertebral cortex causing direct trauma to the spinal cord or injury to nearby nerves (para-spinal nerves, nerve roots, etc) during positioning.

Pedicle screws are inserted into the spinal pedicle, the bony process projecting backward from the vertebral body, and stabilized with connecting rods or plates placed longitudinally with regard to the vertebrae. Biomechanical tests of pedicle-screw constructs have demonstrated the critical importance of screw placement in the isthmus of the pedicle to obtain proper cortical purchase necessary to resist screw pullout. Thus, surgical pedicle screw placement is technically demanding. Extensive training and meticulous attention to detail are required to avoid injuring the patient.

Despite the surgeon's skill, misplaced pedicle screws are common. Consequently, a number of computer-assisted surgical navigation systems and intraoperative fluoroscopy techniques have been developed to increase the accuracy rate of pedicle screw placement; however, these imaging systems have certain drawbacks. Fluoroscopic procedures increase radiation exposure to the patient, the operating room personnel, and the surgeon. Computer-assisted navigation systems require a pre-operative CT scan, exposing the patient to additional radiation and some surgeons perceive it as too time consuming and complicated to justify its routine use. Oftentimes, these imaging systems are limited in terms of resolution, that is, a breach of the medial wall of the pedicle may not be detectable.

While all of the aforementioned systems may enable a surgeon to determine if the screw has in fact breached the pedicle wall, this breach or crack is discovered only after the bone screw has been implanted. This requires the withdrawal and re-insertion of the screw after it may have already caused damage. Disruption of the pedicle wall by the installation equipment (K-wires, distractor systems, drill bit, awl, curette, etc) does not usually cause neural deficit. A minor crack or breach created by the installation equipment may not be detectable by an electronic test probe placed inside the pedicle screw opening. Most significant nerve damage occurs during the process of implanting the pedicle screw into the bony structure. During installation of the pedicle screw, a portion of the screw may inadvertently contact the nerve through the breach created by the installation equipment. This can give rise to neurological trauma, sensory deficit, or pain. Consequently, a need exists in the surgical arts for a system capable of providing proper fastener placement during implantation process to actively negotiate around or past nerves to prevent damage or improper screw placement.

PRIOR ART

U.S. Pat. No. 2,704,064, to Fizzell et al., discloses a device called a neurosurgical stimulator which is used to distinguish nerves. The device comprises two probes that are placed on the body in an area to be stimulated and the operating surgeon watches for a response to the applied current (twitching). If a response is observed, the surgeon avoids cutting in that particular area to prevent inadvertent damage to a nerve. For example, the device is useful for tumor excision as it is capable of distinguishing tumor tissue from the surrounding nerves. Function of the Fizzell device is dependent upon manual adjustment of the electric current and the visual observations of the user. This requires that the surgeon continuously observe the muscular response; however, when anaesthesia is used the muscular response may be attenuated to a point where the muscular response isn't perceivable by the surgeon. Thus, the surgeon using this device may still damage the nerve.

U.S. Pat. No. 5,284,153, to Raymond et al., discloses a method in which a nerve stimulator is used to locate, identify the function of, and guard against the inadvertent cutting of nerves during surgical procedures. The nerve locator includes a surgical probe which is coupled to an electrical source, a device for detecting responses of the nerve to electrical stimuli and means for automatically modulating the magnitude of the stimulus.

U.S. Pat. Nos. 5,196,015, and 5,474,558, both to Neubardt, disclose a system and procedure for spinal pedicle screw insertion to reduce the likelihood of nerve damage caused by improper screw placement. A screw opening is started in part of a skeletal region, e.g., a pedicle of a lumbar vertebra and an electric potential of a certain magnitude is applied to the inner surface of the opening while the patient is observed for nervous reactions such as leg twitching. The opening continues to be formed while the electric potential is applied until a desired hole depth is obtained in the absence of nervous reaction to the potential. The direction in which the screw opening is being formed is changed to a direction other than the last direction, after observing patient reactions to the electric potential when the screw opening was being formed in the last direction. The '558 patent further discloses a tool that includes a handle and detachable installation equipment (probe member, tapping member and driver) extending from the handle for forming an opening in bone tissue, tapping, and inserting the screw, respectively. Stimulator circuitry arranged inside the handle produces an electric potential of a predetermined level. Unlike the present invention, the electrical potential is applied to the detachable installation members, not the implant itself. Therefore, the installation equipment measures the distance between the equipment and a proximate nerve. This can create in a proximity gap between the installation equipment and the implant tip which could result in an implant that is dangerously close to or impinging a neural structure.

U.S. Pat. No. 6,796,985 to Bolger et al., discloses a method and equipment for drilling bone, in particular for setting a pedicle screw. The equipment includes a drilling instrument, a source of electric impulses and a connector for connecting the electric impulse source to the drilling instrument. The equipment also includes at least one sensor for detecting a muscle signal either implanted in a muscle or placed on the skin in the vicinity of a muscle before and during drilling. An alert is produced in the event of detection by at least one sensor of a muscle signal correlated with the source of electric impulses connected to the drilling instrument. Unlike the present invention, the implant in the '985 patent does not include at least one electrically conductive region capable of providing a stimulation signal used to test the integrity of the bony structure (e.g., pedicle) and location of any proximal neural structures as it is being implanted therein.

U.S. Pub. No. 2005/0149035, to Pimenta et al., discloses a surgical access system including a tissue distraction assembly and a tissue retraction assembly, both of which may be equipped with one or more electrodes for use in detecting the existence of (and optionally the distance and/or direction to) neural structures before, during, and after the establishment of an operative corridor to a surgical target site. Similarly, U.S. Pub. No. 2005/0075578 to Gharib et al., discloses systems and related methods for performing surgical procedures and assessments, including the use of neurophysiology-based monitoring to: (a) determine nerve proximity and nerve direction to surgical instruments employed in accessing a surgical target site; (b) assess the pathology (health or status) of a nerve or nerve root before, during, or after a surgical procedure; and/or (c) assess pedicle integrity before, during or after pedicle screw placement.

Unlike the present invention, the electrodes for providing stimulation to a given nerve are located on the surgical accessories in both Pimenta et al., and Gharib et al. The surgical accessories refer to the devices or components used to create an operative corridor to the surgical target site (e.g., K-wires, dilating cannula systems, distractor systems and/or retractor systems) or for assessing pedicle integrity (via a screw test probe). This system also provides a proximity gap between the location of the anode(s) on the accessories and the implant, which could result in an implant residing dangerously close to or impinging a neural structure. In addition, the pedicle test probe is able to apply a stimulation signal to test the integrity of the medial wall of the pedicle only after the pedicle screw has been fully implanted into the bony structure. Conversely, the present invention teaches at least one electrically conductive region formed on the distal end of the implant itself. This difference is critical since these electrically conductive regions are able to apply a stimulation signal to test the integrity of a bony structure and/or proximity (direction, distance) of neural structures as the implant is being secured in situ. Thus, any neural structures exposed by the surgical accessories or those undetected by the surgical accessories may be still be avoided prior to any neurological trauma being done.

SUMMARY OF THE INVENTION

The purpose of this invention is to provide an implant suitable for neurophysiological monitoring of a target implant site. The implant includes a body member having a proximal and distal end, wherein the distal end is constructed and arranged to secure to a surgical target site. The distal end includes at least one region constructed and arranged to emit an electrical potential in an amount effective to generate a stimulating electrical signal in any proximally located neural structure. The stimulating electrical signal provides the distance and/or direction of the neural structure relative to the distal end during securement of the implant in vivo. Thus, the implant may be maneuvered during surgery such that any neural structure may be avoided.

Accordingly, it is an objective of the instant invention to provide an implant constructed and arranged for securement to a surgical target area whereby any neural structures located proximate to or at the target area may be avoided.

Another objective of the instant invention to provide a system that minimizes neural damage, thereby providing less post-operative pain.

Yet another objective of the present invention is to teach an implant system with an alarm means that utilizes audio and/or visual feedback to indicate to the surgeon when the implant is close to the neutral structures.

Still a further objective of the invention is to teach an implant which allows for shorter surgery, decreased x-ray exposure, and fewer complications for the patient.

Another objective of the present invention is to teach an implant system simple enough to ensure the surgeon will routinely use it.

Other objectives and advantages of the instant invention will become apparent from the following description taken in conjunction with the accompanying drawings wherein are set forth, by way of illustration and example, certain embodiments of the instant invention. The drawings constitute a part of this specification and include exemplary embodiments of the present invention and illustrate various objects and features thereof.

DETAILED DESCRIPTION OF THE INVENTION

Figure 1:
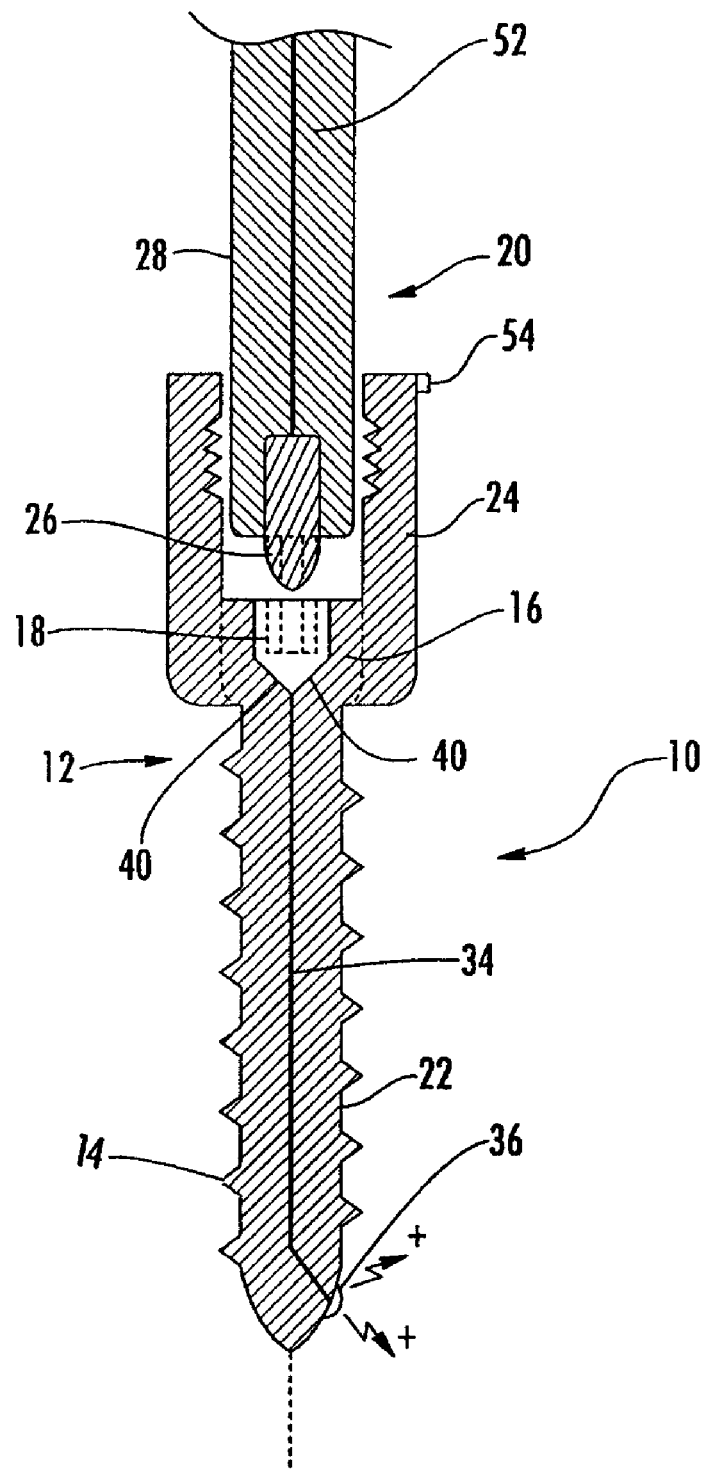
FIG. 1 is a cross-sectional view of a fixed axial bone screw in accordance with one embodiment of the present invention.

For the purposes of promoting an understanding of the principles of the invention, reference will now be made to the embodiments illustrated in the drawings and specific language will be used to describe the same. However, the illustrated embodiments are merely exemplary. It is understood that no limitation of the scope of the invention is thereby intended. Any alterations and further modifications in the illustrated devices, and such further application of the principles of the invention as illustrated herein are contemplated as would normally occur to one skilled in the art to which the invention relates.

Figure 2:
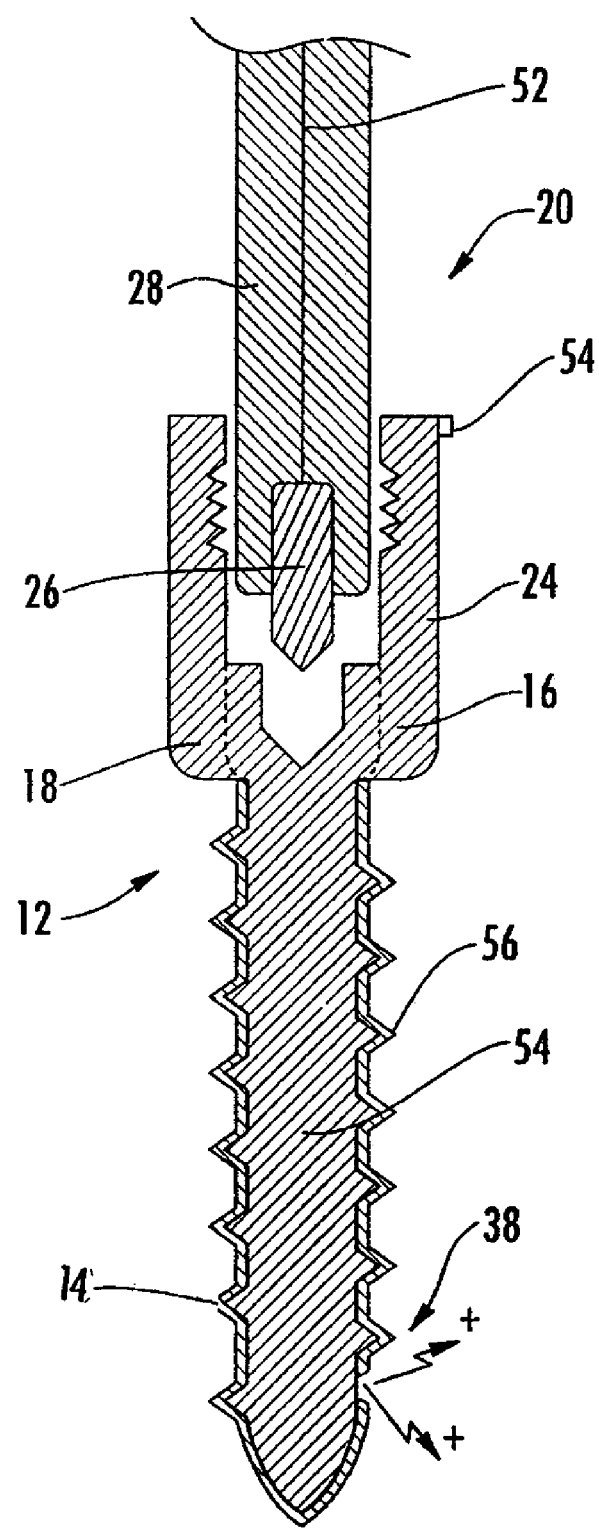
FIG. 2 is another cross-sectional view of a fixed axial bone screw in accordance with another embodiment of the present invention.
Figure 3:
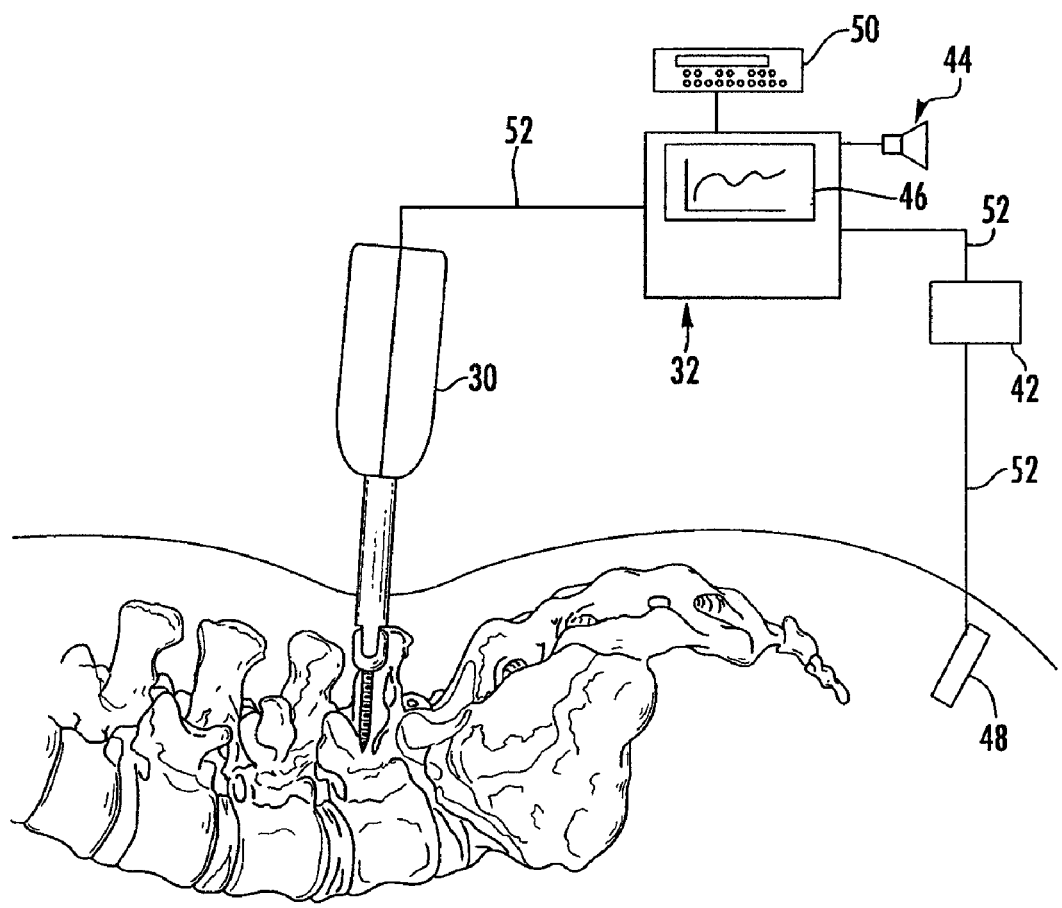
FIG. 3 is a lateral view of the lumbar spinal region and a bone screw driver in communication with components of a nerve stimulator used to carry out implantation of the implant.

Referring now to FIGS. 1-3 which illustrate the implant 10 of the present invention suitable for neurophysiological monitoring of a target site, wherein like elements are numbered consistently throughout. FIG. 1 shows one non-limiting example of an implant, depicted here as fixed-axial pedicle or bone screw. The bone fastener body includes a proximal end 12 and a distal end 14. The proximal end includes head portion 16 with a tool opening 18 configured to receive any suitable driving tool 20. The distal end includes a threaded shank 22 designed to rotatably engage bone at a selected target site located inside the body of a patient, e.g. isthmus of the pedicle (see FIG. 3). At least a portion of the pedicle screw body is made from a surgically implantable and electrically conductive material including, but not limited to, titanium, stainless steel, or the like.

The bone fastener shown here is a fixed axial screw wherein the proximal end of the screw includes a connector portion 24 fixedly connected to the head portion of the screw. However, a multi-axial screw could be used without departing from the scope of the invention. That is, the connector is capable of 360 degree rotation relative to the threaded shank of the screw along the longitudinal axis L of the shank and angular motion defined by the angle. One example of a suitable multi-axial screw is described in U.S. Pat. No. 5,797,911, herein incorporated by reference. Moreover, the shank of the anchor member may or may be not be cannulated, as is known in the art.

The connector portion 24 of the screw is constructed and arranged to form a passageway designed to removably receive at least one biocompatible stabilizing members (not shown) e.g., interconnecting rod or plate. The connector portion includes an opening constructed and arranged to receive a set screw (not shown), as is known in the art. For example, the set screw may be threadably lowered along the longitudinal axis of the connector portion of the screw to form the passageway. The passageway is narrowed until the exterior surfaces of the biocompatible device are sandwiched between the screw head and the set screw. This acts to reliably secure the biocompatible device onto the screw.

As discussed above, the implant body is made from an electrically conductive material, such as titanium, stainless steel, or other suitable biocompatable conductive metallic material of sufficient strength to engage bone. The opening in the bone may be previously formed using any suitable technique and device, such as a drill, awl, or curette. In addition, the opening may or may not be tapped prior to insertion of the bone fastener. The bone fastener is inserted into the opening in the pedicle by any suitable driving tool 20, (e.g., screw driver). Driving tools are well known in the surgical arts and are used to rotatably secure the bone fastener to the desired position within the opening formed in the pedicle.

As discussed above, the head portion of the bone fastener includes a tool opening 18 configured to receive any suitable driving tool. According to the present invention, the driving tool is in electrical communication with a nerve simulator and used to deliver an electrical potential along the electrically conductive material 34 of the bone fastener to its distal end. For example, the driving means may include a electrically conductive tip 26 (hex head, flat head, or phillips head) designed to correspond with the tool opening in the head of the screw. The head of the screw may include at least one electrical contact 40 designed to mate with the conductive tip of the driving means. The conductive tip 26 may be protected by an insulated shaft 28 connected to a handle 30 which the surgeon grips. The conductive tip is then placed into the head of the bone fastener.

The distal end of the screw includes at least one region constructed and arranged to emit the electrical potential produced in the nerve simulator. For example, electrically conductive region may include a non-insulated, electrically conductive region 38 (FIG. 2), or a least one electrode 36 (FIG. 1), or the like. The electrical potential emitted from the distal end of the screw will produce a stimulating electrical signal in any proximally located neural structure. Alternatively, the anode may extend along at least a portion of the length of an outer surface of the implantable device for stimulation of neural structure(s).

The electrically conductive material of the bone fastener is used to establish electrical communication between the driving means and the distal end. This may be accomplished by any suitable means. For example, a lead wire or otherwise electrically conductive material 34 (titanium, steel, etc) starting at from the head of the bone fastener along the longitudinal axis L of the screw and terminating at the portion of the distal end where the electrical potential is emitted. For example, the conductive core material may be electrically coupled to at least electrode 36, preferably an anode, used to deliver the electrical potential charge to any proximately located neural structure (e.g., nerve).

The stimulating electrical signal produced by the nerve stimulation monitoring device 32 is then detected by a suitable response detecting device 42 in communication therewith, as is known in the art. Although shown in FIG. 3 as separate, the response detecting device may be integrated with the nerve stimulation monitoring device 32, see FIG. 3. Thus, nerve stimulation monitoring device 32 is capable of generating and detecting and/or recording the stimulating signal evoked in the neural structure itself (nerve action potentials) or within the fibers of associated skeletal muscle (muscle action potentials). Examples of some nerve stimulation monitoring devices 32 include, albeit it not limited to, electromyography (EMG) unit, somatosensory (SSEP) unit and/or motor evoked potentials (MEP) unit as known in the art.

Using standard techniques, these devices are connected to the patients via patches or probes 48, and capable of providing visual alarm messages on a user display 46 or and/or audible alarms 44 as an indication that the magnitude of the simulating electrical signal exceeds a predetermined threshold. The presence of a neural structure near the distal end of the implant (e.g., tip of the pedicle screw) is measured by the response detecting device once the electrically conductive region simulates, i.e., depolarizes a nearby nerve. As the bone fastener is advanced through the pedicle, the stimulus necessary to elicit an EMG response will vary with distance from the nerve. That is, the closer the electrically conductive region is the to the neural structure, the less stimulus intensity will be required to elicit an stimulating response detected by the patches or probes. The stimulating signal can be measured and monitored by a computer algorithm in the nerve stimulation monitoring device or alternatively may be monitored by a Neurophysiology technician using traditional EMG monitoring equipment. In response, the algorithm will automatically modulate the magnitude of the electrical potential supplied to the implant according to the distance to the nerve. In addition, the nerve stimulation monitoring device should include controls 50 that allow the surgeon or Neurophysiology technician to selectively moderate the amount of electrical potential utilized to generate the simulating electrical signal. The simulating electrical signals are then monitored and assessed by the detector unit to provide the nerve proximity and/or nerve direction. When the distal portion of the screw stimulates a neural structure, this indicates that the neural structure is in front of the advancing fastener. Thus, the distal portion of the bone fastener or implant can be positioned to avoid the structure.

As discussed above, the nerve stimulation monitoring device is in communication with the response-detecting means and the driving tool used to deliver the electrical current to the conductive bone fastener. Any means for providing electrical communication 52 to and from the various devices may be used (wires, cable, etc). Electrical communication is established between the nerve simulation monitoring device unit and the implant once the driving means is placed into the corresponding tool opening at the proximal end of the screw. Although depicted in FIG. 3 as a separate external unit, the nerve stimulation monitoring device may be integrated with the driver tool as disclosed in U.S. Pat. Nos. 5,196,015 and 5,474,558.

According to another embodiment shown in FIG. 2, the bone fastener body (i.e., the shank 22 and head 16) is formed from an electrically conductive material 54 and is electrically insulated with a coating 56, with the exception of at least one electrically conductive region 38 located at the distal end. Since this region is not electrically insulated, it is able to emit the electrical potential therefrom. The conductive material of the bone fastener may be electrically insulated by a non-conductive material, such as epoxy resin, ceramic, polyethylene, or any other biocompatible material that has electrical insulating properties. This embodiment insures that the source of the electrical potential is isolated to the distal end of the screw which allows for the determination of the proximity as well as direction of any nearby neural structure.

In order to determine the direction of the neural structure in any of the aforementioned embodiments, the bone fastener body should include a single electrically conductive region or electrode disposed at the distal end that corresponds to the location of an identifiable mark 54. The identifiable mark should be constructed and arranged so that it remains visible by the surgeon during the implantation process, shown here located on the connector portion of a fixed axis bone fastener. The nerve stimulation monitoring device will provide the electrical potential in a periodic or continuous manner to the electrically conductive region (electrode) while the implant is being secured by rotation into the target site (e.g., bony structure). As the bone fastener rotates, changes (e.g., strength) in the stimulating electrical signal detected by the nerve stimulation monitoring device will indicate the direction of the neural structure relative to the electrode and corresponding reference mark.

Although the invention is described with reference to bone fasteners, specifically a pedicle screw, commonly used for the stabilization and fusion of adjacent spinal vertebrae, it is hereby contemplated that any type of biocompatible implant that may effect neurologic function could be used at any joint found in the human or animal body. Non-limiting examples of other implants include intervertebral inserts, disc prostheses, or the like.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An implant suitable for neurophysiological monitoring of a target site, said implant comprising:
   a body member having a proximal and distal end, said distal end of said body member being threaded, wherein said distal end is constructed and arranged to secure to a target site, said distal end of said body member including an electrically non-conductive coating on substantially the entire external surface of said distal end, an electrically conductive region penetrating through said electrically non-conductive coating, said electrically conductive region positioned on said external surface of said distal end off-center of a longitudinal axis of the body member, said body member being electrically conductive and providing an electrically conductive pathway extending between said proximal end and said electrically conductive region, said electrically conductive region constructed and arranged to emit an electrical potential in an amount effective to generate a stimulating electrical signal in a proximally located neural structure;
   wherein said stimulating electrical signal indicates the proximity of said neural structure relative to said distal end such that said neural structure may be avoided at said target site;
   wherein said at least one electrically conductive region of said implant is in electrical communication with a nerve stimulation monitoring device for providing said electrical potential and controlling the amount of said electrical potential.

2. The implant as set forth in claim 1, wherein said implant is a pedicle screw.

3. The implant as set forth in claim 1, wherein said stimulating electrical signal in said neural structure is detected by an electromyography unit.

4. The implant as set forth in claim 1, wherein said simulating electrical signal in said neural structure is detected by a somatosensory monitoring device.

5. The implant as set forth in claim 1, wherein said stimulating electrical signal in said neural structure is detected by a motor evoked potentials device.

6. The implant as set forth in claim 1, wherein said at least one electrically conductive region is an electrode.

7. The implant as set forth in claim 6, wherein said electrode is an anode.

8. The implant as set forth in claim 1, wherein rotation of said implant body indicates the direction of said neural structure relative to said distal end.

9. The implant as set forth in claim 1, wherein said implant is in electrical communication with an alert means whereby an alert is produced when the magnitude of said stimulating electrical signal exceeds a predetermined threshold.

10. A bone fastener for detecting at least one proximally located neural structure comprising:
    a rotatable fastener body constructed and arranged for engagement with a bony structure, said fastener body having an electrically non-conductive coating on substantially the entire external surface of said fastener body, an electrically conductive region penetrating through said electrically non-conductive coating, said electrically conductive region positioned on said external surface of said fastener body off-center of a longitudinal axis of the fastener body, said fastener body being electrically conductive; and
    at least one anode positioned within said electrically conductive region, said at least one anode constructed and arranged to enable electrical connectivity with a nerve stimulation monitoring device through said fastener body;

wherein rotation of said fastener body within said bony structure is effective for moderating electrical stimulation of said proximally located neural structure;

whereby moderation of said stimulation is indicative of either the proximity of said neural structure relative to said body, or bony structure integrity;

wherein said at least one electrically conductive region of said implant is in electrical communication with a nerve stimulation monitoring device for providing said electrical potential and controlling the amount of said electrical potential.

11. The bone fastener as set forth in claim 10, wherein said fastener is a multi-axis pedicle screw.

12. The bone fastener as set forth in claim 10, wherein said fastener is a fixed axis pedicle screw.

13. The bone fastener as set forth in claim 1, wherein said bone fastener includes an identifiable mark on said proximal end of said body member, said identifiable mark axially aligned with said electrically conductive region.

* * * * *

UNITED STATES PATENT AND TRADEMARK OFFICE
CERTIFICATE OF CORRECTION

| | | |
|---|---|---|
| PATENT NO. | : 7,981,144 B2 | Page 1 of 1 |
| APPLICATION NO. | : 11/534129 | |
| DATED | : July 19, 2011 | |
| INVENTOR(S) | : Christopher Walsh and Wyatt Drake Geist | |

It is certified that error appears in the above-identified patent and that said Letters Patent is hereby corrected as shown below:

Title Page, Item (12), "Geist et al.", should read -- Walsh et al. --.

On the Title Page, Item (75) Inventors: should appear as follows:

-- Christopher Walsh, Parkland, FL (US);
  Wyatt Drake Geist, Davie, FL (US) --

Signed and Sealed this
Twenty-seventh Day of September, 2011

David J. Kappos
*Director of the United States Patent and Trademark Office*